United States Patent [19]
Glenn

[11] Patent Number: 5,707,867
[45] Date of Patent: *Jan. 13, 1998

[54] ANTIVIRAL COMPOUNDS

[75] Inventor: Jeffrey S. Glenn, Palo Alto, Calif.

[73] Assignee: The Regents of the University of California, Oakland, Calif.

[*] Notice: The term of this patent shall not extend beyond the expiration date of Pat. No. 5,605,828.

[21] Appl. No.: 565,085

[22] Filed: Nov. 30, 1995

Related U.S. Application Data

[63] Continuation of Ser. No. 144,759, Oct. 27, 1993, abandoned.
[51] Int. Cl.$^6$ ............................. C12N 5/00; A01N 43/72; A01N 43/90
[52] U.S. Cl. ............................. 435/375; 514/183
[58] Field of Search ............................. 435/235.1, 236, 435/5, 6, 375; 536/6.5; 514/183

[56] References Cited

U.S. PATENT DOCUMENTS

| | | | |
|---|---|---|---|
| 5,196,437 | 3/1993 | Starzl et al. | 514/294 |
| 5,238,689 | 8/1993 | Dwyer et al. | 424/617 |
| 5,308,847 | 5/1994 | Calne | 514/262 |

OTHER PUBLICATIONS

Bartz, S.R. et al., "Inhibition of human immunodeficiency virus replication by nonimmunosuppressive analogs of cyclosporin A," *Proc. Natl. Acad. Sci. USA* 92:5381–5385 (Jun. 1995).

Billich, A. et al., "Mode of Action of SDZ NIM 811, a Nonimmunosuppressive Cyclosporin A Analog with Activity against Human Immunodeficiency Virus (HIV) Type 1: Interference with HIV Protein–Cyclophilin A Interactions," *Journal of Virology* 69(4):2451–2461 (Apr. 1995).

Cote, P.J. et al., "Cyclosporin A Modulates the Course of Woodchuck Hepatitis Virus Infection and Induces Chronicity," *The Journal of Immunology* 146(9):3138–3144 (May 1, 1991).

Damaso, C.R.A. et al., "Cyclosporin A inhibits vaccinia virus replication in vitro," *Arch Virol* 134:303–319 (1994).

Glenn, J.S. et al., "In Vitro–Synthesized Hepatitis Delta Virus RNA Initiates Genome Replication in Cultured Cells," *Journal of Virology* (1990) 64(6):3104–3107.

Glenn, J.S. et al., "Trans–Dominant Inhibition of Human Hepatitis Delta Virus Genome Replication," *Journal of Virology* (1991) 65(5):2357–2361.

Gruber, A. et al., "Reactivation of chronic hepatitis C after withdrawal of immunosuppressive therapy," *Journal of Internal Medicine* 234:223–225 (1993).

Karpas, A. et al., "Inhibition of human immunodeficiency virus and growth of infected T cells by the immunosuppressive drugs cyclosporin A and FK 506," *Proc. Natl. Acad. Sci. USA* 89:8351–8355 (Sep. 1992).

Kondo, Y. et al., "Effect of Hexamethylene Bisacetamide and Cyclosporin A on Recovery of Herpes Simplex Virus Type 2 form the in Vitro Model of Latency in a Human Neuroblastoma Cell Line," *Cancer Research* 50:7852–7857 (Dec. 15, 1990).

Lykavieris, P. et al., "HBV Infection in Pediatric Liver Transplantation," *Journal of Pediatric Gastroenterology and Nutrition* 16:321–327 (1993).

Onyekaba, C.O. et al., "Persistent infection of mice by lactate dehydrogenase–elevating virus: effects of immunosuppression on virus replication and antiviral immune responses," *Virus Research* 14:297–316 (1989).

Rosnewirth, B. et al., "Inhibition of Human Immunodeficiency Virus Type 1 Replication by SDZ NIM 811, a Nonimmunosuppressive Cyclosporine Analog," *Antimicrobial Agents and Chemotherapy* 38(8):1763–1772 (Aug. 1994).

Suresh, M. et al., "Hemorrhagic enteritis virus induced changes in the lymphocyte subpopulations in turkeys and the effect of experimental immunodeficiency on viral pathogenesis," *Veterinary Immunology and Immunopathology* 45:139–150 (1995).

Wang et al. "In Vitro Effect of FK506 on Lymphocyte Activation and Viral Replication in Chronic Hepatitis 13 Carriers", Hepatology, vol. 16 (4 part 2), Abst. 292A, 1992.

Shiraki et al. "Effect of FK506 on Replication of Human Cytomegalovirus In Vitro," J. Antibiot., vol. 44, No. 5, pp. 550–552, 1991.

*Primary Examiner*—David Guzo
*Attorney, Agent, or Firm*—Morrison & Foerster LLP

[57] ABSTRACT

The macrolide FK506, produced by Fujisawa Pharmaceuticals is effective in inhibiting the replication of hepatitis D virus. It is believed that replication is inhibited either by virtue of the ability of FK506 to inhibit proline isomerase or otherwise to interfere with the function of a C-terminal proline in a replication factor or by virtue of its interference with RNA replication directly.

5 Claims, 1 Drawing Sheet

ANTIVIRAL COMPOUNDS

This application is a File Wrapper continuation of application Ser. No. 08/144,759, filed Oct. 27, 1993, now abandoned.

This invention was made with government support under grant no. AI-22470 awarded by the National Institutes of Health. The government has certain rights in this invention.

TECHNICAL FIELD

The invention is directed to inhibitors of viral replication. In particular, it concerns the use of compounds related to the immunosuppressant macrolide FK506 to interfere with replication.

BACKGROUND ART

The macrolide FK506, which is of the formula:

is manufactured by Fujisawa Pharmaceutical Company Limited, and is a known immunosuppressant. It is a member of class of immunophilins described by Schreiber, S. L. in *Science* (1991) 251:283–287. Other members of this class include rapamycin, cyclosporin A, and an additional macrolide designated 506BD. However, the present applicant is unaware of any suggestion that FK506, which is also known to be a proline isomerase (or rotamase) inhibitor, or the other compounds described in this article would have antiviral activity. Unexpectedly, FK506 was found to be capable of inhibiting hepatitis Delta virus (HDV) replication.

U.S. Pat. No. 5,196,437 describes the ability of compounds related to FK506 to regenerate liver which has been negatively affected by hepatitis B and non A/non B. However, this appears to be unconnected with any direct effect on the virus.

DISCLOSURE OF THE INVENTION

The invention is directed to a method to inhibit viral replication illustrated by the ability of FK506 to inhibit hepatitis D virus replication. The surprising ability of FK506 to do this suggests that replication of a variety of viruses which share features with HDV may be inhibited by compounds related to FK506, provided at least one of several specific conditions is met. FK506 is known to have proline isomerase inhibiting activity. HDV antigen behaves as a transcription factor (defined herein as a protein that plays a key role in nucleic acid polymerization) and contains a C-terminal proline essential for replication, independent of the preceding amino acid sequence. Therefore, the ability of FK506 to inhibit HDV replication suggests that compounds which inhibit proline isomerases or which otherwise interfere with the function of a C-terminal proline in an essential replication factor will inhibit replication of viruses that replicate via at least one such transcription factor.

Accordingly, in one aspect, the invention is directed to a method to inhibit viral replication which method comprises contacting a virus or a cell in which a virus replicates, where the virus contains at least one transcription factor which has a C-terminal proline, with an effective amount of at least one proline isomerase inhibitor such as FK506 or of an inhibitor of proline recognition or function. In another aspect, the invention is directed to a method to inhibit viral replication wherein the virus, like HDV, replicates through an RNA intermediate, which method comprises contacting the target virus or a cell in which the virus replicates with FK506 or its acyl esters.

MODES OF CARRYING OUT THE INVENTION

Figure 1:
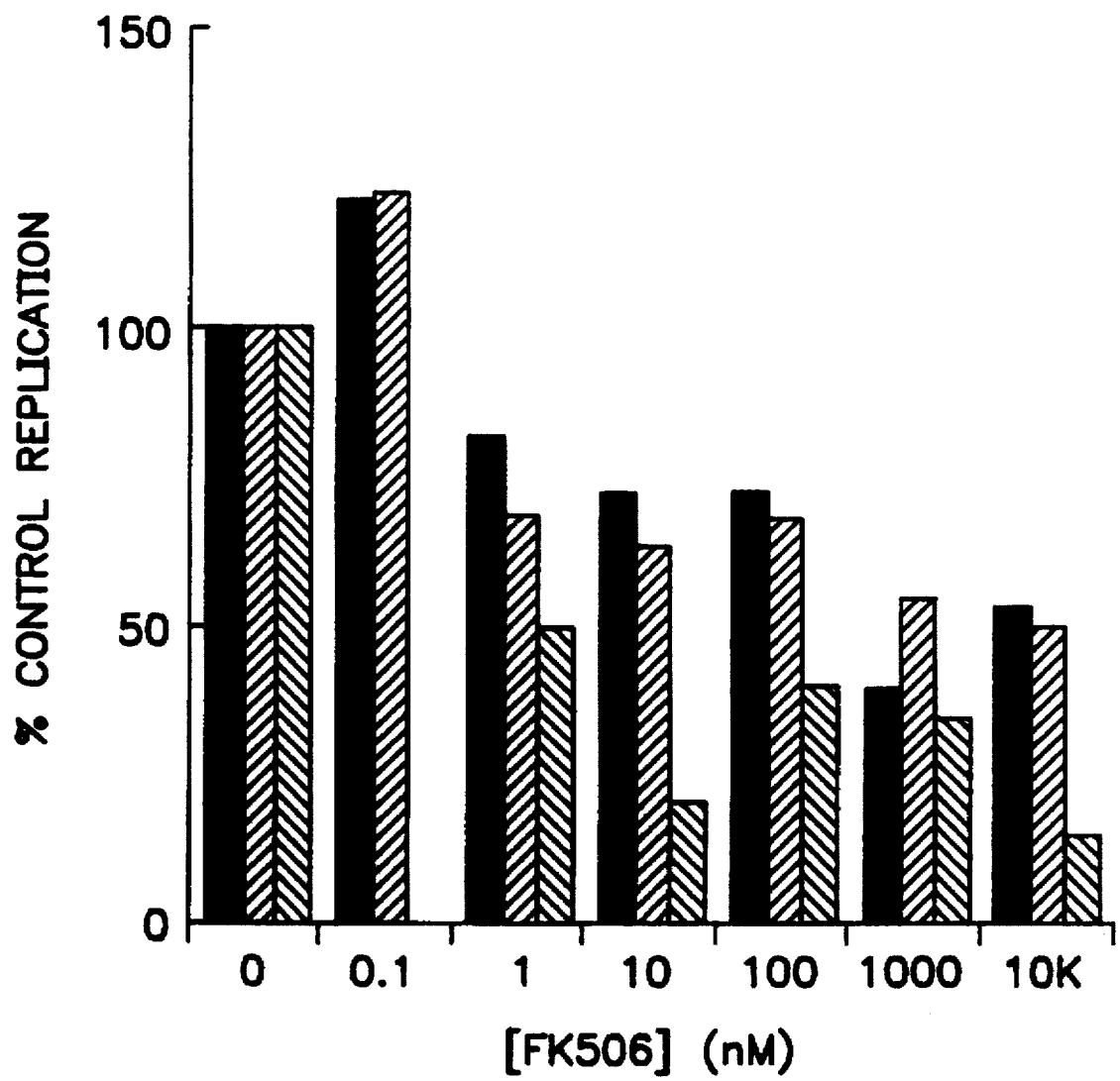
FIG. 1 is a bar graph showing the effect of FK506 on HDV gene replication.

In the illustration below, it is demonstrated that FK506, a proline isomerase inhibitor, is capable of inhibiting HDV genome replication. This surprising result leads to the conclusion that viruses which replicate in a manner similar to HDV will be similarly affected by compounds related to FK506. The features of HDV replication which are significant for interaction with FK506 include replication through an RNA intermediate and/or the presence of an essential transcription factor having a C-terminal proline.

Viruses known to replicate through an RNA intermediate include those belonging to the picornavirus, togavirus, bunyavirus, orthomyxovirus, paramyxovirus, rhabdovirus, retrovirus, arenavirus, and hepatitis B virus families.

Viruses known to contain an essential transcription factor with a C-terminal proline include human adenovirus, feline leukemia virus, vaccinia virus, papilloma virus, hepatitis C virus, hepatitis B virus, human immunodeficiency virus, varicella zoster virus, and bunyavirus.

For any proposed target virus, the ability to ascertain these features is within the skill of the art and provides a basis for concluding or not concluding that the relevant class of antiviral compounds will be effective.

FK506 has the structure set forth in the Background section above. FK506 contains three free hydroxyl groups; each hydroxyl group independently may be esterified with an acyl group of 1–6C. By "acyl (1–6C)" is meant a saturated or unsaturated moiety of the formula RCO wherein R is saturated or unsaturated hydrocarbyl. Typical such acyl groups include acetyl, penten-1-oyl, propanoyl, 2-methyl propanoyl and the like.

Proline isomerase inhibitors other than FK506 include rapamycin, cyclosporin A, 506BD and their acyl derivatives. All of these compounds are useful in the invention.

The following example is intended to illustrate but not to limit the invention.

EXAMPLE 1

Inhibition of HDV with FK506

HDV gene replication was assayed by the method of Glenn, J. S., et al. *J Virol* (1991) 65:2357–2361. FK506 was supplied at various concentrations into the replication assays.

One day post delivery of S-genome RNA to GAG cells, the GAG cells were split equally into 60 mm dishes, which were maintained at specific concentrations of FK506 ranging from 0.1 nM to 10 μM until harvest on day 7. The harvested RNA was assayed by Northern blot to detect HDV genome replication. The Northern blots include a control probe for host cell RNA (Signal Recognition Particle Receptor mRNA) to permit normalizing total RNA levels. Phosphoimaging analysis permitted sensitive quantitation and comparison of levels of viral replication.

The results of three experiments are shown in FIG. 1; each bar reflects the level of HDV genome replication at the indicated drug concentration. The solid and striped columns represent results from duplicate dishes showing the degree of variability. The stippled columns represent results obtained in a previous experiment conducted two months previously when the drug was freshly constituted.

The results show that nM concentrations of FK506 achieve about 50% inhibition of HDV replication.

I claim:

1. A method to inhibit the replication of a virus that requires proline isomerase for replication, said method comprises the step of contacting a cell in which said virus replicates with an amount of a proline isomerase inhibitor sufficient to inhibit replication.

2. A method to inhibit the replication of a virus that requires proline isomerase for replication, said method comprises the step of contacting a cell in which said virus replicates with an amount of a compound of the formula:

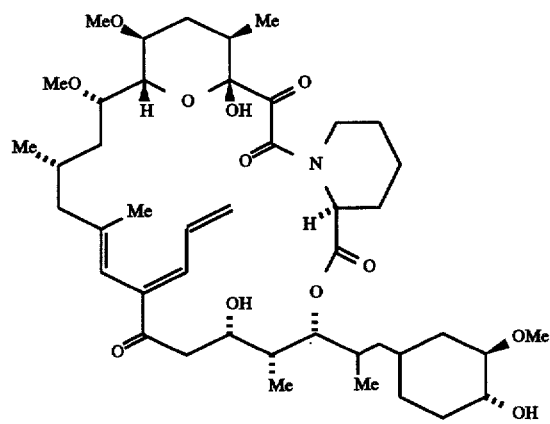

or a pharmaceutically acceptable acyl (1–6C) ester thereof sufficient to inhibit replication.

3. A method to inhibit the replication of a virus that requires proline isomerase for replication, said method comprises the step of contacting a cell in which said virus replicates with an mount of a compound selected from the group consisting of FK506 rapamycin and 506BD sufficient to inhibit replication.

4. A method to inhibit the replication of hepatitis D virus, said method comprises the step of contacting a cell in which said virus replicates with an amount of a proline isomerase inhibitor sufficient to inhibit replication.

5. A method to inhibit the replication of hepatitis D virus, said method comprises the step of contacting a cell in which said virus replicates with an amount of a compound of the formula:

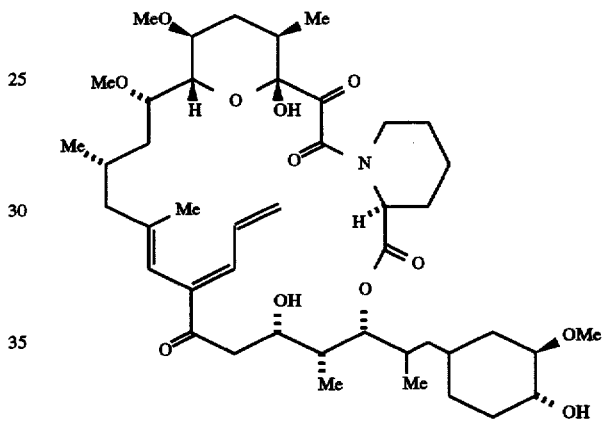

or a pharmaceutically acceptable acyl (1–6C) ester thereof sufficient to inhibit replication.

* * * * *